United States Patent

Katz

Patent Number: 5,989,254
Date of Patent: Nov. 23, 1999

[54] PEDICLE SCREW ASSEMBLY

[76] Inventor: Akiva Raphael Katz, 4 Elgin Road, Milnerton, 7441, Western Cape Province, South Africa

[21] Appl. No.: 09/081,036

[22] Filed: May 18, 1998

[30] Foreign Application Priority Data

May 20, 1997 [ZA] South Africa ............................ 97/1149

[51] Int. Cl.⁶ .................................................... A61B 17/56
[52] U.S. Cl. ............................................... 606/73; 606/72
[58] Field of Search ................................. 606/71, 72, 73, 606/74, 75, 69, 70, 88; 623/17

[56] References Cited

U.S. PATENT DOCUMENTS

| | | | |
|---|---|---|---|
| 5,474,555 | 12/1995 | Puno et al. ................................... | 606/73 |
| 5,690,630 | 11/1997 | Errico et al. ................................. | 606/73 |
| 5,733,286 | 3/1998 | Errico et al. ................................. | 606/73 |
| 5,782,833 | 7/1998 | Haider ......................................... | 606/73 |
| 5,797,911 | 8/1998 | Sherman et al. ............................. | 606/73 |

*Primary Examiner*—Michael Buiz
*Assistant Examiner*—(Jackie)Tan-Uyen T. Ho
*Attorney, Agent, or Firm*—McAulay Nissen Goldberg Kiel & Hand, LLP

[57] ABSTRACT

A pedicle screw assembly consists of a screw having a part spherical head providing a saddle shaped contact surface for a connecting rod, the head is held in a coupling member allowing limited angular movement between the screw and coupling member in one plane only and this plane is at right angles to the contact surface. Surfaces are provided in the connecting member for supporting a connecting rod, which is securable in the coupling member by a cap engaging in the coupling member to clamp the connecting rod against the supporting surfaces while still enabling the screw to move angularly with respect to the coupling member.

20 Claims, 2 Drawing Sheets

PEDICLE SCREW ASSEMBLY

FIELD OF THE INVENTION

This invention relates to a pedicle screw assembly for use mainly in human spinal correction systems.

BACKGROUND TO THE INVENTION

Multi-segmental spinal fixation is an accepted surgical procedure in the treatment of disorders of the spine. It involves the use of a series of pedicle screws and connecting rods and its efficacy is to a large extent dependant on the ability of the screw assemblies to accommodate rigidly a rod bent to the contour of the spine.

OBJECT OF THE INVENTION

Many different assemblies are produced to achieve this result and it is the object of the present invention to provide an assembly which is simple to use and achieves the desired results in an effective and efficient manner.

SUMMARY OF THE INVENTION

According to this invention there is provided a pedicle screw assembly comprising a screw threaded shank with a head at one end shaped to seat in and extend into a coupling member in a manner permitting limited relative angular movement between the coupling member and the shank in one plane only, the coupling member extending beyond the head as a cylindrical sleeve longitudinally slotted partway down its length from its free end so that the base of the slot provides oppositely disposed bearing surfaces for a connecting rod, the head shaped within the coupling member to provide a locating surface for the connecting rod and a driving tool engagement formation; and a removable locking cap in screw threaded engagement with the outer end of the coupling member.

Further features of this invention provide for the head and coupling member to be complementarily part spherical in shape with the shank projecting from the coupling member through a groove provided to permit the angular movement, for the shank to have oppositely disposed flats adjacent the head which bear against the side of the groove to prevent movement of the shank about its axis in the coupling member and for the driving tool engagement formation to be provided a pair of oppositely disposed flat surfaces extending parallel to the connecting rod locating surface.

The invention also provides for the locking cap to include a screw threaded stem engaging in a thread within the coupling member and a collar located around the coupling member.

Still further features of the invention provide for the cap and coupling member to have complementary buttress threads, for the shank of the screw to be tapered, for the thread to be self tapping and for the free end to have a rounded point.

Yet further features of this invention provides for the head and coupling member to be retained together by a radial pin extending through the coupling member into the head and for the coupling member to have external flats formed thereon to be engaged by a suitable spanner.

BRIEF DESCRIPTION OF THE DRAWINGS

These and other features of this invention will become apparent from the following description of one embodiment of the invention in which reference is made to the accompanying drawings in which.

DETAILED DESCRIPTION WITH REFERENCE TO THE DRAWINGS

Figure 1:
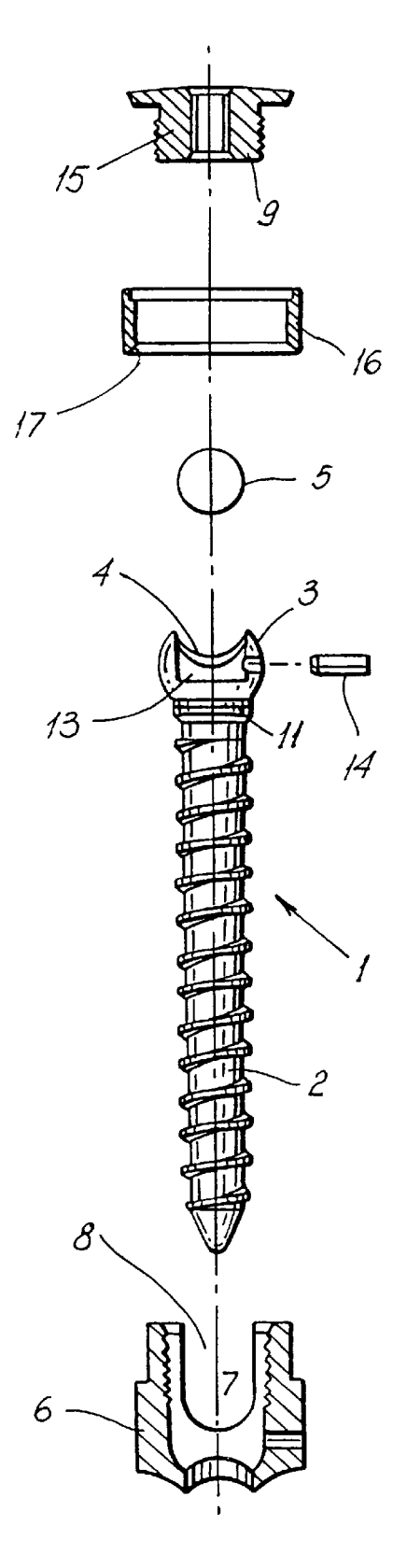
FIG. 1 is an exploded view of the assembly.
Figure 2:
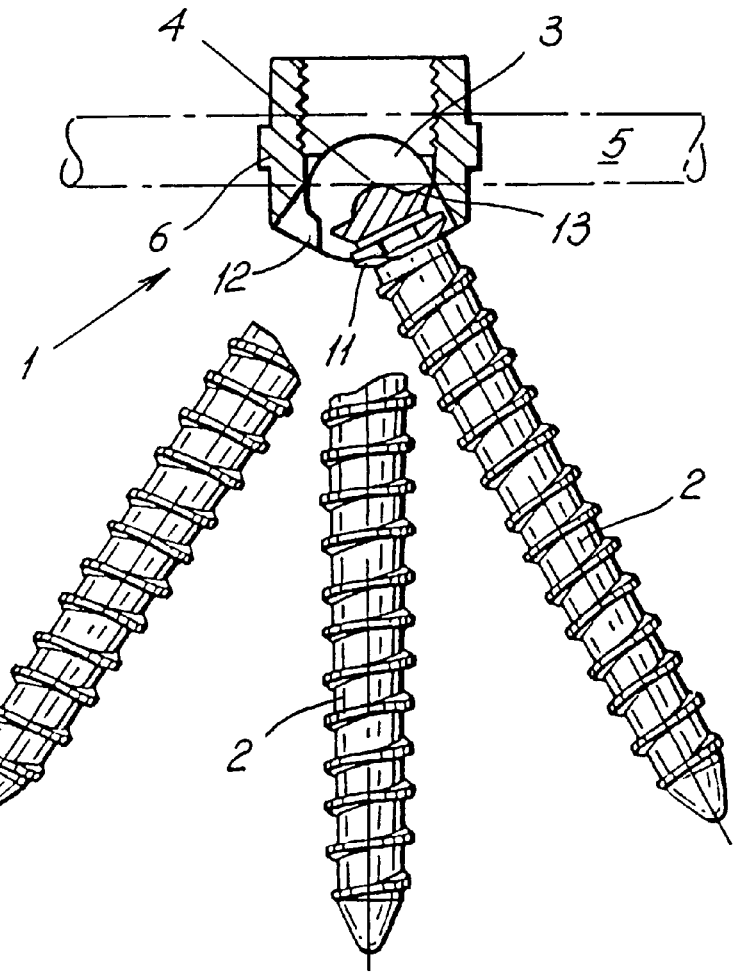
FIG. 2 is a view of the assembly with the components at right angles to the positions shown in FIG. 1.

As illustrated a pedicle screw assembly (1) has a screw (2) which has a part spherical head (3) on the free end of which is formed a saddle shaped locating surface (4). This surface in use locates against a connecting rod (5) for connecting a series of screw assemblies together in use.

The head is embraced by a coupling member (6). The coupling member (6) extends as a cylindrical sleeve (7) and has a part spherical constriction at one end forming a seat for the head (3) of the screw. A slot (8) extends from the opposite end diametrically across the coupling member (6) to accommodate the to connecting rod (5) to be used with the screw assembly (1). The base of the slot (8) provides oppositely disposed bearing surfaces which support the connecting rod (5). The outer end of the sleeve (7) is screwthreaded to be engaged by a cap (9). This is described in more detail below.

Figure 3:
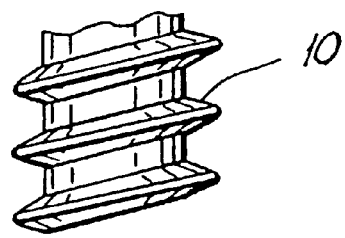
FIG. 3 shows a detail of the screw thread.
Figure 4:
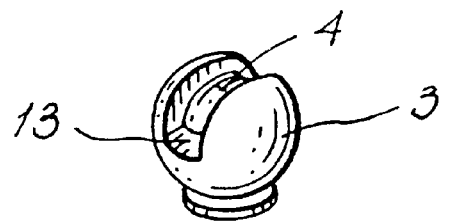
FIG. 4 shows a detail of the screw head.

The shank of the screw (2) has a rounded point at its free end and carries a special self tapping thread formation (10) which is illustrated in FIG. 3. The end of the shank adjacent the head (3) tapers outwardly towards the head. The shank has adjacent the head, a pair of parallel flat surfaces (11) which co-operate with those provided by the sides of the groove referred to below. This prevents relative rotational movement between the coupling member (6) and the screw (2) about the axis of the screw.

The thread construction illustrated ensures in use, firm engagement in human bone.

The outer part of the coupling member (6) adjacent the screw shank is grooved at (12) and this allows limited angular movement of the screw (2) relative to the coupling member (6) in a plane though the axis of the associated connecting rod (5) with the sides of the groove guiding the flat surfaces (11) on the shank of the screw. This movement is such that the shank may pass through an angle of the order of 30°.

Also to enable this movement to take place with the screw assembly in use, the head is embraced in the coupling member (6) which has an inner surface of complementary shape to the contacting part of the head (3) and the head (3) and coupling member (6) are shaped such that with the head positioned in the coupling member the contacting surface (4) is located at right angles to the slot (8) and thus the length of the connecting rod (5).

The head (3) is also shaped so that the jaw of a driving tool can be inserted into the coupling member to engage over the free end of the head to drive the screw, in use, into bone formation. To enable this to be done flat surfaces (13) are provided which extend from and parallel to the locating surface (4).

To assist in inserting the screw into the appropriate bone in use, the coupling member (6) is retained on the screw head (3) by means of a pin (14) inserted through a radial hole in the coupling member (6) into the head (3) to be retained by frictional engagement. The pin (14) is positioned so that the angular movement between the screw and coupling member can take place.

This ensures that the connecting rod (5) can be located through the coupling member (6) supported in the desired angular position relating to the screw shank.

The connecting rod will be similarly positioned in a second screw assembly to fix a particular spinal segment.

The cap (9) has a screw threaded stem (15) which is screwed into the connecting member (6) to lock the pedicle screw assembly in position in use. The cap (9) will have a socket formed therein to receive the end of a fastening tool. This enables the cap to secure the assembly together. To simultaneously hold the coupling member and ensure that it is prevented from splaying a collar (16) is fitted around the outer part of the coupling member. Also the screw threads are buttress threads which reduces radial loading on the connecting member as the components are secured in position.

With the components assembled as above described the contact surface (4) on the end of the screw holds the screw (3) and connecting rod (5) so that there can be no axial movement of the screw (3) relative to the connecting rod (5) and coupling member (6). While preventing this movement it is nevertheless possible to obtain the angular movement between connecting rod (5) and coupling member (6) as is necessary to achieve segmental spinal fixation. To enable the necessary contact to be obtained with various positions of the screw relative to the coupling member the contact surface conforms to the saddle shape illustrated.

Also the dimensions of the collar (16) and stem (15) are chosen so that when the stem (15) contacts the connecting rod (5) the end of the collar (16) will also press into the connecting rod and prevent any axial movement of the rod relative to the screw.

Under the operating conditions encountered when pedicle screws are inserted the area around the screw is usually very confined. Thus the possibility of using a fastening tool within the confines of the coupling member (6) has very material advantages. Similarly to assist in locating the cap assembly a lead-in (17) is provided in the collar (16) which facilitates proper alignment of the cap and engagement of the screw threads. Flat surfaces will be provided on the outside of the coupling member to be engaged by a spanner during the securing of the assembly.

The tapering of the shank of the screw outwardly towards the head imparts added strength to the screw.

What I claim as new and desire to secure by letters:

1. A pedicle screw assembly comprising
    a screw threaded shank with a head at one end shaped to seat in and extend into a coupling member in a manner permitting only limited relative angular movement between the coupling member and the shank in one plane only
    the coupling member extending beyond the head as a cylindrical sleeve longitudinally slotted partway along its length from its free end so that
    the base of the slot provides oppositely disposed bearing surfaces for a connecting rod,
    the head shaped within the coupling member to provide a locating surface for the connecting rod and a driving tool engagement formation; and
    a removable locking cap in screw threaded engagement with the outer end of the coupling member.

2. A pedicle screw assembly as claimed in claim 1 wherein the head and coupling member are complementarily part spherical in shape.

3. A pedicle screw assembly as claimed in claim 1 wherein the shank projects from the coupling member through a groove which permits the relative angular movement.

4. A pedicle screw assembly as claimed in claim 3 in which the shank has oppositely disposed flats which bear against the sides of the groove.

5. A pedicle screw assembly as claimed in claim 1 wherein the driving tool engagement formation is provided by a pair of oppositely disposed flat surfaces extending parallel to the connecting rod locating surface.

6. A pedicle screw assembly as claimed in claim 1 wherein the locking cap includes a screw threaded stem engaging in a thread within the coupling member.

7. A pedicle screw assembly as claimed in claim 6 wherein there is a collar located around the coupling member.

8. A pedicle screw assembly as claimed in claim 6 wherein the screw threads are buttress threads.

9. A pedicle screw assembly as claimed in claim 1 wherein the screw shank is tapered outwardly towards the head and the free end has a rounded point.

10. A pedicle screw assembly as claimed in claim 1 wherein the screw head and coupling member are retained together by a radial pin extending through the coupling member into the head.

11. A pedicle screw assembly as claimed in claim 1 wherein spanner engageable flats are provided on the coupling member.

12. A pedicle screw assembly as claimed in claim 1, in which the shank has oppositely disposed flats which bear against the sides of a groove in the coupling member to prevent relative rotational movement between the coupling member and the screw.

13. A pedicle screw assembly as claimed in claim 1, including a collar located around the coupling member.

14. A pedicle screw member as claimed in claim 1, wherein the screw threads are buttress threads.

15. A pedicle screw assembly as claimed in claim 2, wherein the shank projects from the coupling member through a groove which permits the relative angular movement.

16. A pedicle screw assembly as claimed in claim 15, wherein the driving tool engagement formation is provided by a pair of oppositely disposed flat surfaces extending parallel to the connecting rod locating surface.

17. A pedicle screw assembly as claimed in claim 16, wherein the locking cap includes a screw threaded stem engaging in a thread within the coupling member.

18. A pedicle screw assembly as claimed in claim 17, wherein the screw shank is tapered outwardly towards the head and the free end has a rounded point.

19. A pedicle screw assembly as claimed in claim 1, wherein the screw head and coupling member are retained together by a radial pin extending though the coupling member into the head.

20. A pedicle screw assembly as claimed in claim 19, wherein spanner engageable flats are provided on the coupling member.

* * * * *